United States Patent [19]

Black

[11] Patent Number: 4,802,987

[45] Date of Patent: Feb. 7, 1989

[54] SELECTIVE PERMEATION OF AROMATIC HYDROCARBONS THROUGH POLYETHYLENE GLYCOL IMPREGNATED REGENERATED CELLULOSE OR CELLULOSE ACETATE MEMBRANES

[75] Inventor: Laura E. Black, Sarnia, Canada

[73] Assignee: Exxon Research and Engineering Company, Florham Park, N.J.

[21] Appl. No.: 583,104

[22] Filed: Feb. 24, 1984

[51] Int. Cl.[4] ............................................ B01D 13/00
[52] U.S. Cl. ..................................... 210/640; 210/653
[58] Field of Search .................... 55/16, 158; 210/640, 210/500.2, 651, 653

[56] References Cited

U.S. PATENT DOCUMENTS

| | | | |
|---|---|---|---|
| 2,947,687 | 8/1960 | Lee | 210/23 |
| 2,958,656 | 11/1960 | Stuckey | 210/23 |
| 2,958,657 | 11/1960 | Binning et al. | 210/23 |
| 2,970,106 | 1/1961 | Binning | 208/347 |
| 3,043,891 | 7/1962 | Stuckey | 260/674 |
| 3,228,877 | 1/1966 | Mahon | 210/651 |
| 3,244,763 | 4/1966 | Cahn | 260/677 |
| 3,335,545 | 8/1967 | Robb et al. | 55/16 |
| 3,410,794 | 11/1968 | Li | 208/308 |
| 3,447,286 | 6/1969 | Dounoucos | 55/16 |
| 3,450,631 | 6/1969 | Bloch et al. | 210/22 |
| 3,494,780 | 2/1970 | Skiens | 117/63 |
| 3,503,186 | 3/1970 | Ward | 55/16 |
| 3,592,672 | 7/1971 | Rowley | 106/189 |
| 3,617,546 | 11/1971 | Li et al. | 210/22 |
| 3,625,734 | 12/1971 | Ward | 117/46 |
| 3,696,028 | 10/1972 | Li et al. | 208/308 |
| 3,772,072 | 11/1973 | Brown et al. | 117/144 |
| 3,844,735 | 10/1974 | Steigelmann et al. | 55/16 |
| 3,873,653 | 3/1975 | Meinecke et al. | 264/41 |
| 3,878,276 | 4/1975 | Hoernschemeyer | 264/41 |
| 3,930,990 | 1/1976 | Brun et al. | 208/308 |
| 4,035,291 | 7/1977 | Chiang et al. | 210/640 X |
| 4,039,499 | 8/1977 | Steigenmann et al. | 260/29.6 |
| 4,060,566 | 11/1977 | Yahnke | 260/677 |
| 4,087,388 | 5/1978 | Jensen et al. | 260/2.5 |
| 4,115,465 | 9/1978 | Elfert et al. | 260/674 |
| 4,154,770 | 5/1979 | Kaplan | 585/332 |

FOREIGN PATENT DOCUMENTS 70084  6/1978  Japan .

OTHER PUBLICATIONS

"Separation of Aromatics and Naphthenes by Permeation Through Modified Vinylidene Fluoride Films", McCandless, Ind. Eng. Chem. Process Dis. Develop., vol. 12, #3, pp. 354–359 (1973).

"Separation of Refinery Streams by Membrane Permeation", Binning et al., Symposium on Less Common Separation Methods in Petroleum Industry, St. Louis Meeting of ACS 3/21-25/1961.

"Membrane Processes in Industry and Biomedicine" (Brier, edtior), Plenum Press, pp. 73–99 (1971).

"Industrial Applications of Facilitated Transport", Kimura et al., Recent Developments in Separation Science, vol. V, pp. 11-25 (1979).

"Synthetic Membranes Containing Schardinger Cyclodetrin Additives", Lee, J. Applied Poly Sci. 26 pp. 489-497 (1981).

"Separation of Liquid Mixtures by Using Polymer Membranes. Permeation of Binary Organic Liquid Mixtures Through Polyethylene", Huang et al., J. Applied Poly Sci., 12, pp. 2615-2631 (1968).

(List continued on next page.)

Primary Examiner—Frank Spear
Attorney, Agent, or Firm—Joseph J. Allocca

[57] ABSTRACT

Aromatic hydrocarbons present in a hydrocarbon feed stream containing a mixture of aromatic hydrocarbons and non-aromatic saturated organic components are separated from said hydrocarbon feed stream by selective permeation of the aromatic hydrocarbon through a regenerated cellulose or cellulose acetate membrane which has been impregnated with polyethylene glycol. The thus treated membrane possesses high selectivity for aromatic hydrocarbons at a high flux. The amount and type of polyethylene glycol impregnated into the membrane is carefully controlled in order to achieve high aromatic selectivity and high flux.

2 Claims, 1 Drawing Sheet

OTHER PUBLICATIONS

"Separation of Hydrocarbons by Selective Permeation Through Polymeric Membranes", Fels & Li, Polymer Sci. Technol #6, pp. 357-373 (1974).

"Immobilized Liquid Membranes", Ward, Recent Developments in Separation Science, vol. 1, pp. 153-161 (1972).

"Polymeric Alloys of Polyphosphonate and Acetyl Cellulose-Sorption and Diffusion of Benzene and Cyclohexane", Cabasso et al., J. Applied Poly Sci. 18, pp. 2117-2136 (1974).

"Separation of Organic Liquid Mixtures by the Permeation Process with Graft Copolymer Membranes", Huang et al., Chem. Eng. Prog. Symp. Ser., vol. 65, #91, pp. 52-58 (1969).

"Ultrafiltration Through Cellophane of Porosity Adjusted Between Colloidal and Molecular Dimensions", McBain et al., J. Phys. Chem 40, pp. 1157-1926.

SELECTIVE PERMEATION OF AROMATIC HYDROCARBONS THROUGH POLYETHYLENE GLYCOL IMPREGNATED REGENERATED CELLULOSE OR CELLULOSE ACETATE MEMBRANES

BRIEF DESCRIPTION OF THE INVENTION

Hydrocarbon feed streams containing aromatic and saturated components are selectively separated into aromatic rich and aromatic lean phases by the selective permeation of the aromatic components through specially treated hydrophilic membranes selected from regenerated cellulose and cellulose acetate under pervaporation conditions. Regenerated cellulose as such has little selectivity for aromatic hydrocarbons in preference to non-aromatic components of a feed stream, and has a low flux. However, it has been discovered that regenerated cellulose membranes can be rendered selective and permeable to aromatic hydrocarbons by impregnating the regenerated cellulose, prior to use, with carefully controlled quantities and types of polyethylene glycol. Similarly, cellulose acetate membranes containing polyethylene glycol exhibit very high selectivities for aromatic hydrocarbons.

In its preferred embodiment, the hydrocarbon feed stream being separated is made up of a mixture of aromatic and saturated hydrocarbons and is most typically a reformate stream such as a gasoline reformate stream. Such streams are presently separated by solvent extraction using solvents such as sulpholane, glycols, $SO_2$, etc or they can be enriched in aromatics by distillation.

The present process employing polyethylene glycol impregnated regenerated cellulose and cellulose acetate membranes can selectively remove aromatics from these mixed feed streams to reduce the severity of solvent extraction or eliminate distillation. This reduces the high energy consumption requirements of the conventional processes augmented or replaced by the membrane separation process.

BACKGROUND OF THE INVENTION

Figure 1:
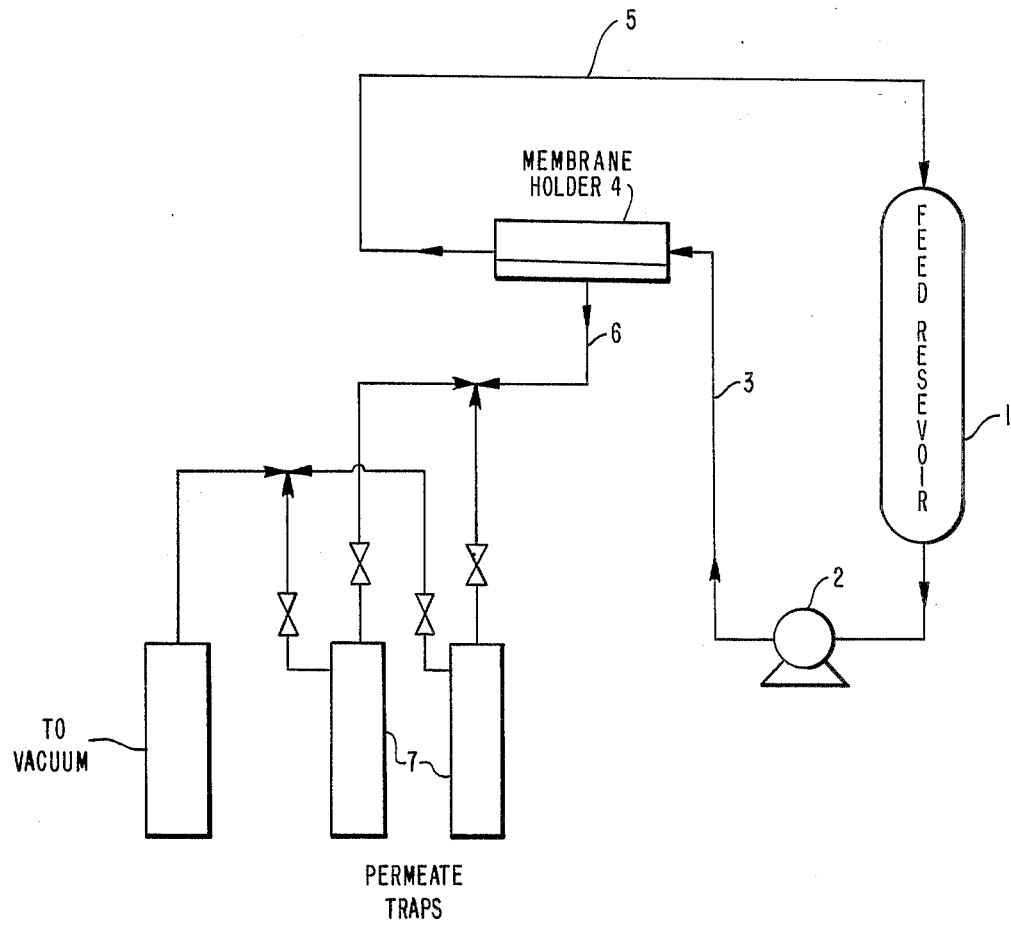
FIG. 1 is a schematic of laboratory unit used to evaluate membranes for the present process.

The separation of aromatics from saturates is desirable in many processes. An increase of aromatics content in reformates leads to a higher octane rating motor fuel. Aromatics are also recovered from other similar streams for the preparation of various arylalkylates and for aromatic solvent production.

The separation of aromatics from saturates is presently achieved using a variety of techniques, e.g., distillation (conventional, vacuum, extractive or azeotropid); solvent extraction using sulpholanes, glycols or $SO_2$; adsorption using molecular sieves such as natural or synthetic zeolites. Other techniques have also been proposed including complexation of aromatics with various chemicals such as cyclodextrins, and membrane separation processes.

Membrane separation processes are attractive due to their simplicity and low energy consumption. In separating aromatics from saturates various constraints are imposed on the membrane process by the very nature of the feed streams involved such as physical and chemical similarities.

In light of these restrictions and obstacles, pervaporation has come to be recognized as a suitable membrane separation process for the separation of aromatics in low molecular weight hydrocarbon streams ($<C_{10}$). Pervaporation is a process in which specific components of a liquid feed stream selectively dissolve into and diffuse through a thin film. Downstream of the film, these components are removed by evaporation from the surface by applying vacuum or sweeping with an inert fluid.

Various polymeric films have been used under pervaporation conditions. These include hydrophobic polymers such as polyethylene, polypropylene and polyvinylidene fluoride, hydrophilic polymers such as ethyl cellulose and cellulose acetate butyrate and aromatic containing polymers such as polyethylene styrene copolymer, aromatic polyurethanes, crosslinked polystyrene, and aromatic polyphosphonate-cellulose acetate polymeric alloys. Separation factors ranged from 1 to 20 and flux ranged from $1\times10^{-2}$ to $1\times10^{-5}$ $m^3/m^2$ day. Aromatic containing polymers generally showed high selectivity for aromatics but had moderate fluxes. (See U.S. Pat. No. 2,970,106; U.S. Pat. No. 3,043,891; U.S. Pat. No. 2,958,656; U.S. Pat. No. 2,947,687; U.S. Pat. No. 2,958,657; German Pat. No. 2,626,629; and U.S. Pat. No. 3,930,990).

The use of liquid membranes to separate aromatics from saturates is an alternative to pervaporation through polymeric films. Liquid membranes are made up of hydrocarbon/surfactant/water emulsions in heavy mineral oils. The hydrocarbon mixture is emulsified in an aqueous phase composed of a surfactant (e.g., saponin), a water soluble polar compound (e.g., glycerol, polyethylene glycol), and water. When this emulsion is dispersed in a heavier oil solvent, stable drops are formed such that the aqueous phase forms a thin film between the two hydrocarbon phases. The glycerol (or PEG) used to increase the drop stability and overall separation efficiency. The glycerol (or PEG) also enhances the solubility of the aromatics in the aqueous phase and hence their migration through the liquid membrane. Separation factors up to 20 have been achieved. The drawbacks of this process are the low stability of the droplets, the complexity of the operation and problems associated with recovery and recycle of the constituents making up the liquid membrane droplets.

To overcome the problems and limitations associated with liquid membranes while taking advantage of their high selectivity, the immobilization of the liquid membranes in a porous matrix was developed. Immobilized liquid membranes are extractive liquids trapped in the porous matrix or on the surface of a solid such as a polymer membrane.

Several methods for immobilizing a liquid in the matrix of a membrane to form an imobilized liquid membranes have been described in the prior art. See for example, Chemistry Letters, 1980, pg. 1445–1448; U.S. Pat. No. 3,625,734; U.S. Pat. No. 4,039,499; "Membranes for Pressure Permeation" by Friedlander and Lutz, Membrane Processes in Industry and Biomedicine, M. Bier, ed., Plenum Press, N.Y.-London 1971 (pg. 73–99); U.S. Pat. No. 3,447,286; U.S. Pat. No. 3,335,545; Recent Developments in Separation Science, Volume I, CRC Press (1973), pg. 153 ff, Recent Developments in Separation Science, Volume V, CRC Press (1979), pg. 11 ff; U.S. Pat. No. 3,450,631; U.S. Pat. No. 4,060,566; Ind. Eng. Chem. Process Dis. Develop 12(3)

1973; Japanese Kokai Sho 53 (1978) 70084. Methods include:
1. Supporting the liquid film on a porous unwet backing.
2. Supporting the liquid film on a non-interacting polymer film.
3. Swelling the polymer film with liquid.
4. Casting the polymer and liquid together into a film.
5. Forming a gel using the liquid.
6. Supporting the liquid film in a porous polymer film.

An immobilized liquid membrane has been used for aromatic/saturate separation by pervaporation. This membrane was prepared by casting a mixture of polyvinylidene fluoride and 3-methyl sulfolane, which is an aromatic extraction agent. (J. of Applied Polymer Science, Volume 26, 489–497 (1981)). Pure polyvinylidene fluoride membranes have high selectivity (18 for benzene/cyclohexane) but low flux (of $10^{-5}$ m$^3$/m$^2$ day at 60° C.). Incorporating 3-methyl sulfolene up to 25 wt.% decreases the selectivity to 8 and increases the flux to $10^{-3}$ m$^3$/m$^2$ day at 60° C.

Schordinger $\alpha$- and $\beta$-cyclodextrins in a hydroxylpropylmethyl cellulose membrane have also been used for the separation of aromatics by pervaporation (J. Applied Polymer Science Volume 26, pg. 489-497 (1981)).

Polyethylene glycol has been extensively used for the treatment of membranes and as an immobilized liquid in various polymeric membranes. Polyethylene glycol and glycerol are used as pore stabilizers for hydrophilic menbranes such as regenerated cellulose and cellulose acetate (U.S. Pat. No. 3,772,072) to prevent drying and pore collapse. Wet membranes from the casting solution are treated with aqueous solutions of PEG or glycerol then dried, leaving PEG or glycerol behind in the pores of the membrane.

Polyethylene glycol has also been used as a substitute for swelling agents or non-solvents in casting solutions for the production of reverse osmosis cellulose acetate membranes (U.S. Pat. No. 3,878,276). Polyethylene glycols have also been used as a plasticizer to improve the flux of low flux cellulose acetate membranes and hollow fibres (U.S. Pat. No. 3,873,653) as well as some other synthetic organic polymer membranes (U.S. Pat. No. 4,087,388).

Several examples of the use of immobilized polyethylene glycol membranes to separate polar gases, e.g., $SO_2$ or $CO_2$ from gaseous mixtures have been demonstrated. Thus polyethylene glycol (MW 300 to 4000) has been cast with cellulose nitrate in tetrahydrofuran solvent to form a membrane used to selectively separate $CO_2$ (Chemistry Letters, 1980, pgs. 1445-1448). An immobilized film of polyethylene glycol was supported on a porous polymer membrane and used to separate $SO_2$ from gas streams (U.S. Pat. No. 3,625,734). Diethylene glycol on a silicon rubber membrane was used to separate $CO_2$ from $O_2$ (U.S. Pat. No. 3,335,545). A rigid gel of polyethylene glycol and Cabosil or Cellosize supported on a porous backing was used for $SO_2$ separation. (Recent Developments in Separation Science, Volume I, CRC Press, 1973 pg. 153 ff). Polyhydridic alcohols, including polyethylene glycol have been immobilized in porous polymer membranes and used to separate unsaturated compounds from a mixture of organic compounds (Japanese 53-70084, 1978). The concept of a semi-permeable membrane extraction using a porous absorbent barrier containing a selective solvent to separate aromatics from saturates (among other things) is described in U.S. Pat. No. 3,244,763.

In summary, aromatic/saturate separation via membranes has been investigated using a variety of techniques. These include pervaporation through a polymeric film, extraction of aromatics from saturates by an emulsified liquid membrane and by pervaporation through immobilized liquid membranes. High selectivities were achieved in some of these cases, but at the expense of low fluxes. The present invention offers the opportunity to attain high selectivities at higher fluxes.

THE PRESENT INVENTION

The present invention relates to a process for the use of hydrophilic polymeric membrane selected from regeneraated cellulose or cellulose acetate, preferably regenerated cellulose, impregnated with from about 5 to 30 wt.% polyethylene glycol having a molecular weight in the range of about 200 to 100,000 under pervaporation conditions to selectively separate low molecular weight aromatic hydrocarbons from saturated hydrocarbons. This separation using the PEG treated membranes is marked by high flux and high separation factors. This process using PEG impregnated hydrophilic membranes will find its broadest application in aromatics separation from reformate streams. Such a separation is important and useful in the production of high octane motor fuels, in the production of aromatic solvents, etc.

It has been discovered that the selectivity and flux of aromatics through the membrane will be affected by varying the weight percent of polyethylene glycol in the membrane, the pore size of the membrane, the molecular weight of the polyethylene glycol, and the temperature.

Membranes suitable for impregnation with polyethylene glycol are hydrophilic in nature such as the previously indicated regenerated cellulose and cellulose acetate membranes. Regenerated cellulose membranes, which offer the strongest hydrogen bonding between the glycol and the polymer are preferred because they resist leaching of the glycol from the membrane.

Hydrophobic membranes do not hydrogen bond polyethylene glycol. The stability of the latter in the membrane matrix is therefore low. These membranes, therefore, are not useful for this invention.

Useful hydrophilic membranes, preferably regenerated cellulose, are generally from about 10 to 25$\mu$ in dry thickness, have molecular weight cut offs as measured using aqueous solutions of from about 10,000 to 50,000. Since the permeation rate of the membrane (flux) is inversely proportional to the membrane thickness, the thinner membranes are preferred. The MWCO of regenerated cellulose membranes may be modified and controlled by pretreatment with pore modifiers such as caustic (eg NaOH) or $ZnCl_2$ solutions prior to impregnation with PEG. This is important to control flux and selectivity as described in detail in the examples presented below. Such treatment increases flux for a given PEG loading, but with an accompanying reduction in separation efficiency.

The molecular weight of the PEG impregnated in the membrane should be in the range of about 200 to 100,000, preferably about 600 to 14,000. The useful concentration range of polyethylene glycol impregnated in the membrane varies from about 5 to 30 wt.%, preferably about 10 to 25 wt.% most preferably about 10 to 15 wt.%. Polyethylene glycol (PEG) impregnated regenerated cellulose membranes, (useful for the separation of aromatics from saturates in the present invention) can be prepared in a number of ways. Regenerated cellulose membranes are typically supplied by the manufacturer plasticized with glycerol or glycerin to prevent the membrane from drying out. This glycerol or glycerin must be removed, as by a water soak, before PEG impregnation. In the preferred method, a commercially available regenerated cellulose membrane, after removal of any glycerol or glycerin plasticizer, is impregnated with PEG by soaking, immersion, dipping, spraying, passage of the glycol across the membrane, etc. Immersion is the preferred method. Typically the membrane is immersed in a PEG solution for a given period of time, generally until equilibrium is reached. Impregnation is a physical and not a chemical phenomenon and neither changes in temperature nor soak duration beyond the point of equilibrium will affect the final loading of PEG in the membrane. The amount of PEG trapped in the membrane (loading levels) is controlled by PEG concentration in the soaking bath solution and immersion time. Once equilibrium is reached, however, immersion for longer times has little effect; PEG loading will remain constant. At high loadings of PEG, smaller pore membranes are more selective to aromatics than larger pore membranes. The critical loading of PEG (i.e., the upper limit above which separation performance falls off) decreases as the pore size of the membrane increases. As the weight percent of PEG in the membrane is increased, the flux is increased and the selectivity is decreased until the critical concentration level is reached. Above the critical concentration level membrane performance falls off. For PEG 600 this critical loading ranges from about 13-25 wt.%, depending on membrane pore size.

Polyethylene glycol impregnated cellulose acetate membranes can be prepared by dissolving the cellulose acetate and the polyethylene glycol in a solvent, such as methylene chloride, casting a thin film of the solution on a suitable substrate or casting plate (e.g., polished metal, glass etc.) and letting the solvent evaporate to produce a clear flexible film.

The reformate streams which may be subject to the process of the present invention employing PEG impregnated regenerated cellulose or cellulose acetate membranes contain aromatic and saturate components, said streams typically being made up of components not greater than $C_9$-$C_{10}$ with molecular weight of not greater than about 150. Reformates may thus be beneficially upgraded by use of the present invention to obtain high octane motor fuels.

By the process of the present invention aromatics are removed from feedstreams at permeation rates on the order of $10^{-2}$ m$^3$/m$^2$ d and separation factors of 7 or more. Flux and separation factors are directly associated with and dependent on pore size of the membrane, PEG molecular weight, PEG loading levels and operating temperatures and pressures. These relationships will be more fully described in the examples below.

The separation is carried out under pervaporation conditions. The feed is in the liquid phase, its temperature and pressure range from 0° to 100° C. and 0 to 1000 PSIG with a more preferred range being 0° to 100° C. and 0 to 500 PSIG. Vacuum is applied downstream of the membrane such that the pressure is less than the equilibrium vapor pressure of the liquid feed. Separation is achieved by molecules diffusing through the membrane under a concentration gradient driving force caused by the downstream vacuum. The flow rate of the feed must be sufficient to ensure that no stagnant layer of feed accumulates over the membrane surface.

A typical laboratory unit for this process is illustrated in FIG. 1. A hydrocarbon feed consisting of aromatic and saturated hydrocarbons is placed in the feed reservoir 1. The feed is circulated across the membrane holder 4 via pump 2 and line 3. The feed returns to the reservoir from the membrane holder via line 5. The membrane holder is of a plate and frame design in which the feed flows across the upper surface of the membrane and the permeate is removed under vacuum from the downstream side of the membrane via line 6. The permeate is trapped under liquid nitrogen in permeate trap 7. By means of valving, alternate permeate samples can be collected.

A more complete demonstration of the process of this invention can be obtained by reference to the following examples which are illustrative only and are not meant to limit the scope of the invention.

EXAMPLE 1

The following example illustrates that hydrophobic polymeric porous membranes are not suitable for this invention. A polycarbonate porous membrane (pore size = 0.2 × 0.04μ) and a polypropylene porous membrane (pore diameter = 0.54μ) were impregnated with PEG 600 by spreading PEG 600 on the surface of the membranes. These membranes were then tested for their selectivity to aromatics under typical pervaporation conditions (upstream pressure = 0 PSIG, downstream vacuum −10 mm Hg) and at 22° C. The feed used was a mixture of toluene/heptane. The results are listed below in Table 1. All of the PEG was leached from the membranes as indicated by the very high fluxes and no selectivity.

TABLE 1

| Membrane | Wt. % Toluene in Feed | Flux m$^3$/m$^2$ Day | S.F.* |
|---|---|---|---|
| Polypropylene | 50 | very high | 1.0 |
| Polycarbonate | 50 | 2.7 | 1.0 |

*S.F. = $\dfrac{\text{(wt. \% toluene)}}{\text{(wt. \% heptane) permeate}} \Big/ \dfrac{\text{(wt. \% toluene)}}{\text{(wt. \% heptane) feed}}$

EXAMPLE 2

The following example illustrates that polyethylene glycol impregnated regenerated cellulose membranes selectively permeate aromatic hydrocarbons under pervaporation conditions and the performance of the membrane depends both on the concentration of PEG in the membrane as well as the pore size of the membranes. In Table 2 is listed the physical characteristics of the regenerated cellulose membranes that were used in these tests. The regenerated cellulose membranes were impregnated with PEG-600 by soaking a wet membrane in aqueous solutions of varying PEG concentrations for varying times. After treatment, the membranes were dried at 60° C. to remove the water. The weight percent PEG-600 in the membrane was measured in the following fashion. After drying in the oven, the membranes were soaked in toluene for fifteen minutes to remove any excess glycol, dried and weighed. The membranes were then soaked in water, dried and reweighed. The difference in weight yields the percentage of PEG in the membrane. Regenerated cellulose membrane type 5 (PM-100 from Enka A.G.) was treated with zinc chloride to enlarge its pores in the following manner. A wet membrane was soaked in a concentrated aqueous solution of zinc chloride at room temperature for 15 minutes. The use of zinc chloride to expand the pores of regenerated cellulose is well known (J. Phys. Chem. 2257 [40] 1936). After this treatment, the membrane was soaked in water for at least one day to remove the zinc chloride. Following this, the membrane was treated with polyethylene glycol in the previously recited manner. These membranes were then tested for their selectivity to aromatics under typical pervaporation conditions, downstream pressure of about 2 to 3 min. Hg, and at 22° C. The feed used was a mixture of toluene/heptane. In none of these runs using PEG-600 impregnated regenerated cellulose was any leaching of the PEG-600 from the membrane observed. The results are listed below in Table 3. Tables 4 and 5 present the results of the investigation of the effect of temperature and aliphatic component concentration in the performance of a PEG 600 impregnated Type 1 (50,000 MWCO) regenerated cellulose membrane while Table 6 and 7 report the effect of temperature and aliphatic compound concentration on the performace of a $ZnCl_2$ treated Type 5 (PM100) regenerated cellulose membrane.

TABLE 2

| Regenerated Cellulose Membrane Type | MWCO | Porosity % | Dry Thickness μm | Pore Size Å ± 2 |
| --- | --- | --- | --- | --- |
| 1 | 50,000 | 16.5 | 25.0 | 29 |
| 2 | 25,000 | 15.5 | 25.0 | 23 |
| 3 | 15,000 | 14.7 | 25.0 | 19.7 |
| 4 (PM-250) | 10–12 × 10³ | 16.8 | 17.5 | 19 |
| 5 (PM-100) | 10–12 × 10³ | 16.3 | 10.0 | 18.5 |

A control blank experiment was performed (repeated in Table 3) using membrane Type 1 (50,000 MWCO) with no PEG-600 present. For that membrane flux was very low and there was no selectivity. The other membrane samples in this example were impregnated with various weight loadings of PEG-600. As can be seen, as the weight percent PEG-600 in each membrane decreased, the flux decreased and selectivity increased until a certain optimum loading level is attained for a given membrane. Further, as the flux rate is inversely proportional to the membrane thickness, it is seen that thinner membranes yield a higher flux for a given PEG loading and selectivity. The flux of Type 4 membranes (PM250 which is about 17.5μ thick) is almost doubled that of Type 3 membrane (25μ thick) for the same value of selectivity and PEG loading (~24%).

TABLE 3

| Membrane Type | Run # | Wt. % PEG 600 In Membrane | Wt. % Toluene Feed | Flux m³/m² day | S.F. |
| --- | --- | --- | --- | --- | --- |
| 1 | a | 0 | 53.9 | 0.001 | 1.0 |
|  | b | 9 | 54.5 | 0.002 | 5.2 |
|  | c | 9 | 52.5 | 0.04 | 2.9 |
|  | d | 11 | 55.9 | 0.039 | 2.0 |
|  | e | 12 | 55.9 | 0.047 | 1.81 |
|  | f | 13 | 55.9 | 0.064 | 1.5 |
|  | g | 11 | 55.9 | 0.087 | 1.5 |
|  | h | 14 | 55.0 | 0.17 | 1.3 |
|  | i | 34 | 50.5 | 0.23 | 1.2 |
| 2 | a | 10 | 55.0 | nil | — |
|  | b | 14 | 54.5 | 0.04 | 2.3 |
|  | c | 24–34 | 50.0 | 0.25 | 1.4 |
| 3 | a | 24 | 50.0 | 0.04 | 2.3 |
| 4 | a | 15 | 55.0 | nil | — |
|  | b | 22 | 55.0 | nil | — |
|  | c | 24 | 54.0 | 0.07 | 2.5 |

TABLE 3-continued

| Membrane Type | Run # | Wt. % PEG 600 In Membrane | Wt. % Toluene Feed | Flux m³/m² day | S.F. |
| --- | --- | --- | --- | --- | --- |
| 5 | a | 17 | 55.0 | nil | — |
| 5 | a | <12.7 | 56.9 | 0.013 | 7.1 |
| $ZnCl_2$ treated | b | 12.7 | 51.8 | 0.013 | 6.0 |
|  | c | 15 | 56.1 | 0.008 | 3.3 |
|  | d | 19 | 53.1 | 0.10 | 2.1 |
|  | e | 26 | 56.0 | 0.14 | 1.7 |
| 5 | a | 19.4 | 48.5 | 0.091 | 2.33 |
| $ZnCl_2$ treated | b | 19.4 | 45.5 | 0.050 | 3.15 |
|  | c | 19.4 | 45.3 | 0.054 | 3.16 |
| (Temp 22° C. | d | 19.4 | 38.1 | 0.038 | .08 |
| Vacuum 3–5 mm Hg) | e | 19.4 | 28.9 | 0.018 | 5.26 |

TABLE 4

TEMPERATURE STUDY

| Temperature °C. | Total Flux kg/m²d | Wt. % Heptane in Permeate | S.F. | Heptane Flux kg/m²d | Toluene Flux kg/m²d |
| --- | --- | --- | --- | --- | --- |
| 23 | 50.2 | 34.0 | 1.53 | 17.1 | 33.1 |
| 29.9 | 72.91 | 36.0 | 1.40 | 26.3 | 46.6 |
| 30.5 | 69.8 | 34.3 | 1.51 | 23.9 | 45.9 |
| 36.8 | 94.9 | 35.6 | 1.43 | 33.8 | 61.1 |
| 40.2 | 92.51 | 35.6 | 1.43 | 32.9 | 59.6 |
| 41.0 | 99.6 | 37.8 | 1.30 | 37.6 | 62.0 |
| 45.0 | 131.7 | 36.9 | 1.35 | 48.6 | 83.1 |
| 45.1 | 123.9 | 35.6 | 1.43 | 44.1 | 78.8 |
| 50.0 | 200.7 | 37.4 | 1.32 | 75.1 | 125.6 |

Membrane = regenerated cellulose MWCO 50,000 impregnated with 12% PEG 600 ± 1%
Feed = 44% heptane/56% toluene

TABLE 5

CONCENTRATION STUDY
Membrane = regenerated cellulose MWCO 50,000 impregnated with 11.1% PEG 600, deviation ± 1.3 wt. %
Temperature = 23° C.
Feed = toluene/heptane

| Wt. % Heptane in Feed | Total Flux kg/m²d | Wt. % Heptane in Permeate | S.F.* | Heptane Flux kg/m²d | Toluene Flux kg/m²d |
| --- | --- | --- | --- | --- | --- |
| 44.1 | 31.7 | 28.3 | 2.00 | 9.0 | 22.7 |
| 54.9 | 18.0 | 36.8 | 2.09 | 6.6 | 11.4 |
| 64.4 | 13.5 | 44.5 | 2.26 | 6.0 | 7.5 |
| 74.0 | 11.0 | 52.0 | 2.58 | 5.7 | 5.3 |
| 85.6 | 7.3 | 70.9 | 2.44 | 5.1 | 2.2 |

*S.F. = $\frac{wt. \% \text{ toluene}}{wt. \% \text{ heptane permeate}} / \frac{wt. \% \text{ toluene}}{wt. \% \text{ heptane feed}}$

TABLE 6

TEMPERATURE STUDY

| Wt. % Heptane Feed | Flux m³/m²d | S.F. | Elapsed Time (hr) | Temperature °C. |
| --- | --- | --- | --- | --- |
| 44.1 | 0.025 | 1.96 | 1 | 26.8 |
| 44.1 | 0.008 | 2.27 | 2 | 26.8 |
| 44.1 | 0.008 | 2.92 | 3 | 26.8 |
| 43.9 | 0.008 | 3.13 | 4 | 26.8 |
| 43.9 | 0.008 | 3.38 | 5 | 26.8 |
| 43.9 | 0.008 | 3.47 | 6 | 26.8 |
| 43.9 | 0.008 | 3.29 | 7 | 26.8 |
| 43.7 | 0.048 | 3.02 | 8 | 35.0 |
| 43.7 | 0.025 | 3.02 | 9 | 35.0 |
| 42.7 | 0.05 | 2.57 | 10 | 50.0 |
| 42.7 | 0.08 | 2.64 | 11 | 50.0 |
| 43.2 | 0.015 | 2.82 | 12 | 27.2 |

Membrane = PM 100, $ZnCl_2$ treat, 14.8% PEG 600, S = 3.1
Feed = Toluene/Heptane
Vacuum = 305 mm Hg

TABLE 7
EFFECT OF FEED CONCENTRATION

| Wt Percent Heptane Feed | X Heptane Feed | Flux M³/m²d | S.F. |
|---|---|---|---|
| 46.9 | 0.448 | 0.099 | 2.11 |
| 51.5 | 0.494 | 0.091 | 2.33 |
| 54.5 | 0.524 | 0.050 | 3.15 |
| 54.7 | 0.526 | 0.054 | 3.16 |
| 61.9 | 0.593 | 0.038 | 4.08 |
| 71.1 | 0.693 | 0.018 | 5.26 |

Membrane: PM 100, ZnCl₂ treat 19.4 wt % PEG 600
Feed: Toluene/Heptane
Temperature: 22° C.
Vacuum: 3-5 mm Hg

EXAMPLE 3

The following example illustrates that polyethylene glycol of molecular weight 200 and diethylene glycol are not stable at room temperature and that their performance in membranes under pervaporation conditions is inferior to the membrane performance of the same membrane impregnated with PEG-600. Regenerated cellulose membranes of Type 1 and a ZnCl₂ treated Type 5 were impregnated with various amounts of PEG, molecular weight 200 and 600. Regenerated cellulose membrane Type 5 treated with ZnCl₂ was impregnated with diethylene glycol. The diethylene glycol rapidly leached from the membrane, causing the membrane to become impermeable as time elapsed. These membranes were tested for their selectivity to aromatics under typical pervaporation conditions at 22° C. The feed was a mixture of toluene/heptane. The results are listed below in Tables 8, 9 and 10. By comparing these results to those in Example 2, it is obvious that the lower molecular glycol impregnated membranes are inferior in comparison to the membranes impregnated with PEG-600.

TABLE 8
POLYETHYLENE GLYCOL IMPREGNATED 50,000 MWCO MEMBRANES (Type 1 RC Membrane)

| Molecular Weight PEG | Wt. % Heptane Feed | Flux m³/m²d | S.F. | Wt. % PEG | Standard Deviation of Wt. % |
|---|---|---|---|---|---|
| 200 | 43.9 | Nil | — | 4.3 | 0.3 |
| | 43.9 | Nil | — | 10.8 | 1.1 |
| | 43.9 | Nil | — | 12.9 | 0.8 |
| | 43.9 | Nil | — | 14.1 | 1.0 |
| | 43.9 | Nil | — | 15.1 | 1.3 |
| | 43.9 | 0.025 | 1.54 | 16.2 | 0.6 |
| | 43.9 | 0.025 | 1.51 | 11.4 | 2.0 |
| | 43.9 | 0.023 | 1.43 | 13.3 | 1.0 |
| | 43.9 | 0.037 | 1.27 | 14.0 | 1.1 |
| | 43.9 | 0.075 | 1.20 | 16.0 | 1.5 |
| | 43.9 | 0.21 | 1.12 | 16.8 | 0.3 |
| | 43.9 | 0.25 | 1.08 | 22.5 | 0.8 |
| 600 | 46.1 | Negligible | 1.05 | 0 | — |
| | 45.5 | 0.002 | 5.2 | 9.3 | — |
| | 43.9 | 0.11 | 1.32 | 14.2 | 0.4 |
| | 45.0 | 0.17 | 1.3 | 13.9 | — |
| | 49.5 | 0.23 | 1.23 | 34 | — |

(T = 293K, Feed = Toluene/Heptane, Vacuum = 3-5 mm Hg)

TABLE 9
POLYETHYLENE GLYCOL PM 100 ZnCl₂ TREAT MEMBRANES (Type 5)

| Molecular PEG | Wt. % Heptane Feed | Flux m³/m²d | S.F. | Wt. % PEG | Standard Deviation of Wt. % |
|---|---|---|---|---|---|
| 200 | 43.9 | Nil | — | 4.2 | 0.7 |
| | 43.9 | Nil | — | 4.4 | — |
| | 43.9 | Nil | — | 5.0 | 1.8 |
| | 43.9 | Nil | — | 18.4 | 0.3 |
| | 43.9 | Nil | — | 22.8 | 2.1 |
| | 43.9 | 0.013 | 1.64 | 20.8 | 0.7 |
| | 43.9 | 0.18 | 1.40 | 33.8 | 8.6 |
| | 43.9 | 0.21 | 1.12 | 24.2 | 1.1 |
| 600 | 43.9 | Nil | — | 8.5 | 0.9 |
| | 43.9 | Nil | — | 8.6 | 0.3 |
| | 43.9 | Nil | — | 14.1 | 0.9 |
| | 43.9 | Nil | — | 16.9 | 0.6 |
| | 48.2 | 0.01 | 5.9 | 12.7 | — |
| | 43.9 | 0.008 | 3.3 | 14.8 | 3.1 |
| | 46.9 | 0.099 | 2.11 | 19.4 | — |
| | 43.9 | 0.14 | 1.7 | 25.6 | 0.2 |

T = 293K, Feed = Toluene/Heptane, Vacuum = 3-5 mm Hg

TABLE 10
DIETHYLENE GLYCOL (DEG) PM 100 ZnCl₂ TREAT MEMBRANES (Type 5)

| Run # | Flux m³/m²d | S.F. | Elapsed Time (hr) | Wt. % DEG | Standard Deviation of Wt. % |
|---|---|---|---|---|---|
| 1 | Nil | — | 1 | 4.3 | 3.3 |
| 2 | Nil | — | 1 | 10.8 | 1.5 |
| 3 | 3.2 × 10⁻² | 1.38 | 1 | 2.6 | 1.2 |
| | Negligible | 2.38 | 2 | | |
| | Nil | — | 3 | | |
| 4 | 5.0 × 10⁻² | 1.15 | 1 | 5.7 | 1.6 |
| | 1.0 × 10⁻² | 1.9 | 2 | | |
| | Nil | — | 3 | | |
| 5 | 1.08 × 10⁻¹ | 1.76 | 1 | 7.4 | 1.3 |
| | — | 1.92 | 2 | | |
| | 3.3 × 10⁻² | 1.92 | 3 | | |
| | 3.0 × 10⁻² | 2.1 | 4 | | |
| | 6.75 × 10⁻² | 2.0 | 5 | | |
| 6 | 1.58 × 10⁻² | 1.51 | 1 | 8.4 | 0.9 |
| | 6.75 × 10⁻³ | 2.27 | 2 | | |
| | 7.25 × 10⁻³ | 2.38 | 3 | | |
| | 5 × 10⁻³ | 2.54 | 4 | | |
| | 6 × 10⁻³ | 2.8 | 5 | | |
| | 2 × 5 × 10⁻³ | 2.8 | 6 | | |
| 7 | 7.5 × 10⁻³ | 1.1 | 1 | 11.2 | 1.2 |
| | 3.75 × 10⁻² | 1.0 | 2 | | |
| | Nil | | | | |

T = 293K, Feed = 43.95 wt. % heptane/56.05 wt. % toluene, Vacuum = 1.3 mm Hg

EXAMPLE 4

The following example illustrates that regenerated cellulose membranes impregnated with polyethylene glycol with higher molecular weights than 600 can be used to separate aromatics from saturates at temperatures higher than room temperature. At temperatures above 50° C., PEG-600 leaches from regenerated cellulose membranes. Higher molecular weight glycols are more resistant to leaching at higher temperatures. In particular, membranes impregnated with PEG 14,000 yielded stable performance at higher temperatures. These membranes were tested for their selectivity to aromatics under typical pervaporation conditions at elevated temperatures. The feed was a mixture of toluene/heptane. The results are listed below in Table 11.

TABLE 11

| Membrane Type | Run # | Temperature °C. | Wt. % PEG-14,000 In Membrane | Wt. % Toluene Feed | Flux m³/m² day | S.F. |
|---|---|---|---|---|---|---|
| 5 | a | 74 | 14 | 55.9 | 0.005 | 3.2 |

TABLE 11-continued

| Membrane Type | Run # | Temperature °C. | Wt. % PEG-14,000 In Membrane | Wt. % Toluene Feed | Flux m³/m² day | S.F. |
|---|---|---|---|---|---|---|
| | b | 78 | 23 | 55.9 | 0.003 | 2.9 |

EXAMPLE 5

The following example illustrates that polyethylene glycol impregnated regenerated cellulose membranes under pervaporation conditions will selectively permeate the aromatics from an actual reformate stream. This example also shows that only aromatics containing up to ten carbons are selectively permeated across these membranes. The membrane used in this example is a type 5 regenerated cellulose membrane, treated with zinc chloride and impregnated with 18% of PEG-600. This membrane was tested for its selectivity to aromatics under typical pervaporation conditions at 23° C. Table 12 lists the compositions of the feed and permeate streams. As seen from the results, aromatics are selectively permeated across the membrane and the overall selectivity to aromatics is close to the value expected for the PEG concentration in this membrane.

TABLE 12

| Component | Wt. % Component in Feed | Wt. % Component in Permeate | S.F. |
|---|---|---|---|
| C3 | .04 | 0.00 | |
| iC4 | 0.43 | 0.02 | |
| nC4 | .95 | .10 | |
| CP | .03 | .03 | |
| iC5 | 2.25 | .57 | |
| nC5 | 1.66 | .70 | |
| Benz | 2.21 | 4.02 | |
| MCP | .54 | .33 | |
| CH | .29 | .15 | |
| iC6 | 4.46 | 2.39 | |
| nC6 | 2.22 | 1.61 | |
| Tol | 20.48 | 28.37 | |
| DMCP | 0.48 | 0.30 | |
| MCH | 0.17 | 0.11 | |
| iC7 | 8.18 | 5.26 | |
| nC7 | 9.26 | 4.55 | |
| A8 | 19.35 | 28.58 | |
| 6N8 | .39 | .17 | |
| 5N8 | .77 | .48 | |
| P8 | 7.33 | 4.7 | |
| A9 | 12.14 | 13.13 | |
| 6N9 | .62 | .35 | |

TABLE 12-continued

| Component | Wt. % Component in Feed | Wt. % Component in Permeate | S.F. |
|---|---|---|---|
| 5N9 | .01 | .01 | |
| P9 | 2.1 | 1.4 | |
| A10 | 1.87 | 1.3 | |
| 6N10 | .02 | .02 | |
| 5N10 | .02 | .02 | |
| P10 | .79 | .68 | |
| A11 | .92 | .64 | |
| Total Paraffins | 39.69 | 21.99 | 0.43 |
| Total Naphthenes | 3.34 | 1.95 | 0.59 |
| Total Aromatics | 56.97 | 75.03 | 2.50 |

EXAMPLE 6

Polyethylene glycol impregnated cellulose acetate membranes were produced by dissolving cellulose acetate (acetyl content 39.8±0.5%, viscosity (ASTM) 3±1 sec) and polyethylene glycol 600 in methylene chloride. A thin film of the solution was cast on a glass plate and the solvent permitted to evaporate to produce a film (20μ thick). The membrane were tested under pervaporation conditions at 50°±1° C. with a feed of 53±1% tolune/47±1% heptane. The results are presented in Table 13 below:

| Film Composition | S.F. | Flux m³/m² · d |
|---|---|---|
| 13% PEG 600 | 12 | $3 \times 10^{-3}$ |
| 16.7% PEG 600 | 7 | $6 \times 10^{-3}$ |
| 20% PEG 600 | 9 | $6 \times 10^{-3}$ |
| 29.9% PEG 600 | 8 | $6 \times 10^{-3}$ |

What is claimed is:

1. A method for separating a feed stream containing a mixture of aromatic and aliphatic hydrocarbons into aromatic rich and aromatic lean streams by selectively permeating, under pervaporation conditions, the aromatic content through a regenerated cellulose or cellulose acetate membrane which has a dry thickness of from about 10 to 25μ and a molecular weight cut-off in the range of from about 10,000 to 50,000, which membrane is impregnated with from 10 to 25 2r% polyethylene glycol having a molecular weight in the range of about 600–14,000.

2. The method of claim 1 wherein the polyethylene glycol has a molecular weight of about 600, the hydrophilic membrane is regenerated cellulose and the membrane is impregnated with from 13–25 weight percent of the polyethylene glycol.

* * * * *